(12) United States Patent
Ho

(10) Patent No.: US 9,897,521 B2
(45) Date of Patent: Feb. 20, 2018

(54) ROTATING DEVICE

(71) Applicants: LITE-ON ELECTRONICS (GUANGZHOU) LIMITED, Guangzhou (CN); Lite-ON Technology Corporation, Taipei (TW)

(72) Inventor: Szu-Hsien Ho, Taipei (TW)

(73) Assignees: LITE-ON ELECTRONICS (GUANGZHOU) LIMITED, Guangzhou (CN); Lite-On Technology Corporation, Taipei (TW)

( * ) Notice: Subject to any disclaimer, the term of this patent is extended or adjusted under 35 U.S.C. 154(b) by 0 days.

(21) Appl. No.: 15/164,898

(22) Filed: May 26, 2016

(65) Prior Publication Data
US 2017/0276579 A1 Sep. 28, 2017

(30) Foreign Application Priority Data

Mar. 28, 2016 (TW) .............................. 105109729 A

(51) Int. Cl.
*G01N 1/38* (2006.01)
*B01F 9/00* (2006.01)
(Continued)

(52) U.S. Cl.
CPC ............. *G01N 1/38* (2013.01); *B01F 9/0001* (2013.01); *B01F 9/002* (2013.01); *B01F 9/003* (2013.01); *B01F 9/0021* (2013.01); *G01N 35/00029* (2013.01); *B01F 7/10* (2013.01); *B01F 7/14* (2013.01); *B01F 2215/0037* (2013.01);
(Continued)

(58) Field of Classification Search
None
See application file for complete search history.

(56) References Cited

U.S. PATENT DOCUMENTS 3,848,796 A * 11/1974 Bull .......................... B04B 5/02
494/11
5,020,297 A * 6/1991 Borie ...................... B65B 43/44
141/130

FOREIGN PATENT DOCUMENTS

| TW | 311101 | 7/1997 |
| TW | M479416 | 6/2014 |
| TW | 201522617 | 6/2015 |

OTHER PUBLICATIONS

"Office Action of Taiwan Counterpart Application", dated Oct. 4, 2016, p. 1-p. 4.

* cited by examiner

Primary Examiner — P. Kathryn Wright
(74) Attorney, Agent, or Firm — JCIPRNET

(57) ABSTRACT

A rotating device includes a carrier, a rotating plate, and a driving unit. The rotating plate rotatably connected with a pivot portion of the carrier contains a test liquid. The rotating plate or the driving unit has a stopping portion. When the driving unit drives the rotating plate to rotate so the stopping portion moves to a first position and interferes with the carrier, the driving unit applies driving force to the pivot portion of the carrier along a first rotation direction through the rotating plate. When the carrier rotates along the first rotation direction and the driving unit applies driving force to the rotating plate along a second rotation direction opposite to the first rotation direction, the rotating plate rotates relative to the carrier, the stopping portion moves to a second position and interferes with the carrier, and the driving unit applies driving force to the pivot portion of the carrier along the second rotation direction through the rotating plate.

12 Claims, 8 Drawing Sheets

(51) Int. Cl.
  *G01N 35/00* (2006.01)
  *B01F 7/10* (2006.01)
  *B01F 7/14* (2006.01)
(52) U.S. Cl.
  CPC .................. *G01N 2001/386* (2013.01); *G01N 2035/00524* (2013.01)

ROTATING DEVICE

CROSS-REFERENCE TO RELATED APPLICATION

This application claims the priority benefit of Taiwan application serial no. 105109729, filed on Mar. 28, 2016. The entirety of the above-mentioned patent application is hereby incorporated by reference herein and made a part of this specification.

BACKGROUND OF THE INVENTION

Field of the Invention

The invention relates to a rotating device and particularly relates to a rotating device for analyzing liquid.

Description of Related Art

In terms of the clinical examination of blood components, there are a variety of blood analyzers that can be used for blood analysis. One method for blood analysis is to put blood and an agent in a rotating plate on a carrier and then drive the carrier and the rotating plate thereon to rotate, so as to mix the blood and the agent to cause a chemical reaction, such that components of the blood can be analyzed by means of optical detection.

In order to quickly and sufficiently mix the blood and the agent, generally the carrier is changed from a rotating state to a stationary state for the user to manually rotate the rotating plate on the carrier to change the direction of the rotating plate, and then the carrier is driven to rotate again. Changing the direction of the rotating plate may improve the efficiency of mixing the blood and agent but it will take extra time. It is also possible to dispose an additional power source (e.g., a motor) in the carrier for driving the rotating plate to rotate so as to change the direction of the rotating plate, but it will increase equipment expenses.

SUMMARY OF THE INVENTION

The invention provides a rotating device for improving working efficiency and reducing equipment costs.

The rotating device of the invention includes a carrier, at least one rotating plate, and a driving unit. The at least one rotating plate is rotatably connected with a pivot portion of the carrier and is for containing a test liquid. The driving unit is connected with the at least one rotating plate. The at least one rotating plate or the driving unit has at least one stopping portion. When the driving unit drives the at least one rotating plate to rotate relative to the carrier so that the at least one stopping portion moves to a first position on the carrier and interferes with the carrier, the driving unit applies driving force to the pivot portion of the carrier along a first rotation direction through the at least one rotating plate and causes the carrier to rotate along the first rotation direction.

In an embodiment of the invention, when the carrier rotates along the first rotation direction and the driving unit applies driving force to the at least one rotating plate along a second rotation direction opposite to the first rotation direction, the at least one rotating plate rotates relative to the carrier, the at least one stopping portion moves to a second position on the carrier and interferes with the carrier, and the driving unit applies driving force to the pivot portion of the carrier along the second rotation direction through the at least one rotating plate and causes the carrier to rotate along the second rotation direction.

In an embodiment of the invention, when the carrier rotates along the second rotation direction and the driving unit applies driving force to the at least one rotating plate along the first rotation direction, the at least one rotating plate rotates relative to the carrier and the at least one stopping portion moves to the first position on the carrier and interferes with the carrier.

In an embodiment of the invention, the at least one rotating plate rotates along a third rotation direction and causes the at least one stopping portion to move to the first position, and the at least one rotating plate rotates along a fourth rotation direction opposite to the third rotation direction and causes the at least one stopping portion to move to the second position.

In an embodiment of the invention, the carrier has at least two stopping surfaces, and when the at least one stopping portion is at the first position on the carrier, the at least one stopping portion is against one of the at least two stopping surfaces and when the at least one stopping portion is at the second position on the carrier, the at least one stopping portion is against the other one of the at least two stopping surfaces.

In an embodiment of the invention, interferences between the at least one stopping portion and the at least two stopping surfaces limits a range of rotation of the at least one rotating plate relative to the carrier.

In an embodiment of the invention, the driving unit includes a rotating member, the rotating member rotates along the first rotation direction to cause the at least one stopping portion to move to the first position, and the rotating member rotates along the second rotation direction to cause the at least one stopping portion to move to the second position.

In an embodiment of the invention, the rotating member includes a first gear and the at least one rotating plate includes a second gear, and the first gear is engaged with the second gear.

In an embodiment of the invention, the driving unit includes a linking rod with two ends pivotally connected with the rotating member and the at least one rotating plate respectively.

In an embodiment of the invention, the driving unit includes a transmission belt, and the transmission belt is connected between the rotating member and the at least one rotating plate.

In an embodiment of the invention, the driving unit includes a base, the base is connected with the rotating member, and the at least one stopping portion is located on the base.

In an embodiment of the invention, the rotating device includes at least one first magnetic member and at least one first attractable member. The at least one first attractable member is attracted by a magnetic force generated by the at least one first magnetic member, the at least one first magnetic member and the at least one first attractable member are disposed on the carrier and the base respectively, and when the at least one stopping portion is at the first position or the second position, the carrier and the base are positioned by the magnetic force between the at least one first magnetic member and the at least one first attractable member.

In an embodiment of the invention, the rotating device includes at least one first magnetic member and at least one first attractable member. The at least one first attractable member is attracted by a magnetic force generated by the at least one first magnetic member, the number of the at least one rotating plate is two, the at least one first magnetic member and the at least one first attractable member are disposed on the two rotating plates respectively, and when the at least one stopping portion is at the first position or the second position, the two rotating plates are positioned by the magnetic force between the at least one first magnetic member and the at least one first attractable member.

In an embodiment of the invention, the rotating device includes at least one first magnetic member and at least one first attractable member. The at least one first attractable member is attracted by a magnetic force generated by the at least one first magnetic member, the at least one first magnetic member and the at least one first attractable member are disposed on the carrier and the at least one rotating plate respectively, and when the at least one stopping portion is at the first position or the second position, the at least one rotating plate is positioned by the magnetic force between the at least one first magnetic member and the at least one first attractable member.

In an embodiment of the invention, the rotating device includes an elastic member. The elastic member is connected between the carrier and the at least one rotating plate, and when the at least one stopping portion is at the first position or the second position, an elastic force of the elastic member positions the at least one rotating plate and when the at least one stopping portion is located between the first position and the second position, the elastic force of the elastic member causes the at least one rotating plate to rotate so that the at least one stopping portion moves toward the first position or the second position.

Based on the above, in the rotating device of the invention, the driving unit drives the rotating plate to rotate and interfere with the carrier, and drives the carrier to rotate through interference between the rotating plate and the carrier or interference between the base of the driving unit and the carrier. Since the carrier has a rotational inertia when rotating, when the driving unit applies driving force to the rotating plate in the direction opposite to the rotation direction of the carrier, the rotating plate and the carrier rotate relative to each other so as to change the rotation direction of the rotating plate on the carrier. Thus, the user is not required to stop the rotation of the carrier to manually change the rotation direction of the rotating plate. Accordingly, the working efficiency is improved. In addition, the user does not need to dispose an additional driving source for driving the rotating plate on the carrier. Therefore, equipment costs are reduced.

To make the aforementioned and other features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
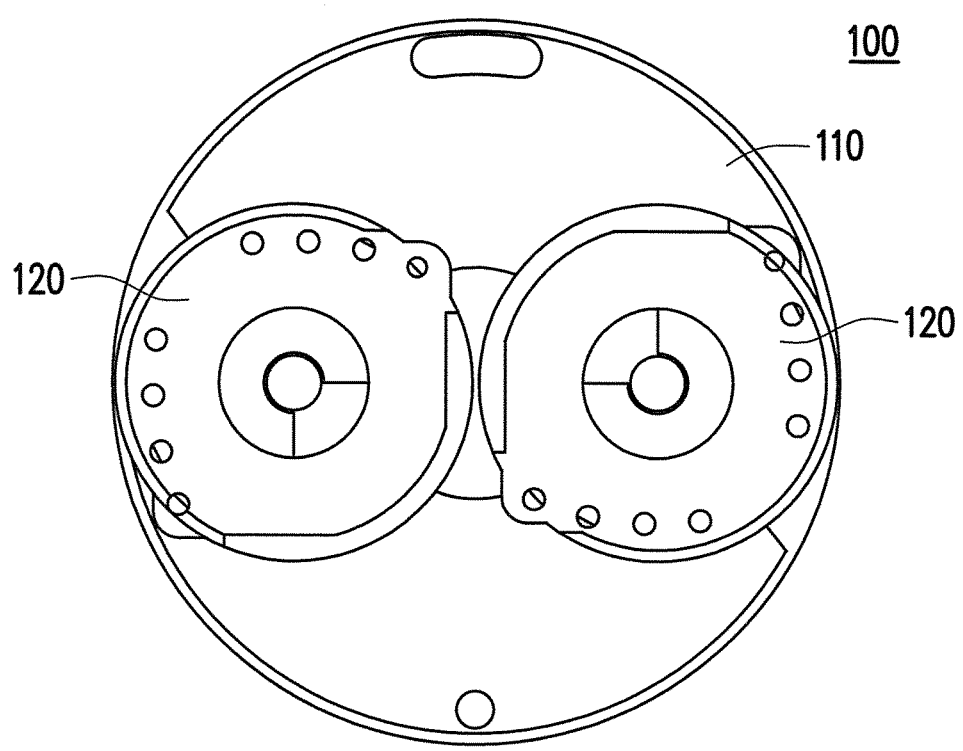
FIG. 1 is a schematic top view of the rotating device according to an embodiment of the invention.
Figure 2:
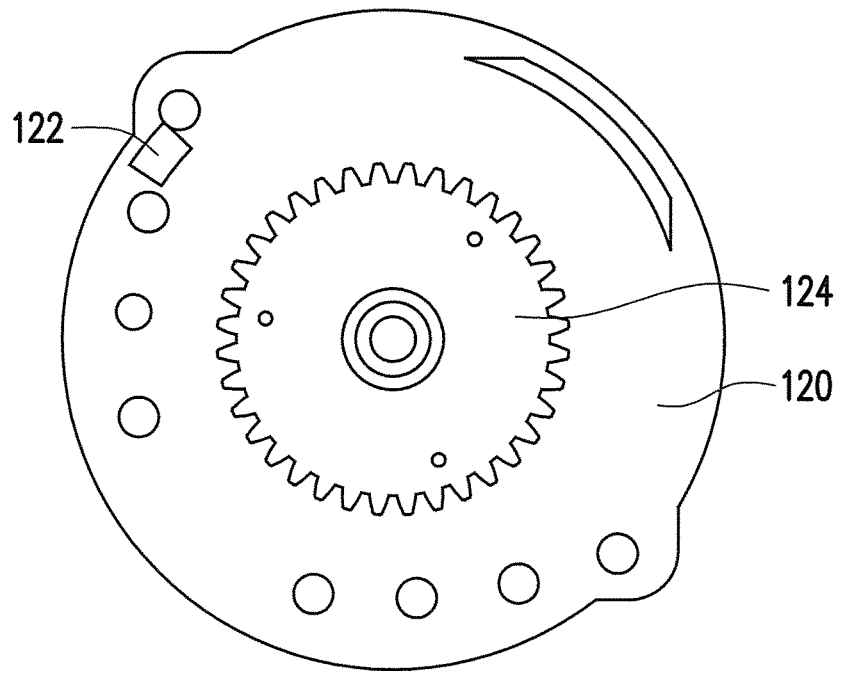
FIG. 2 is a schematic bottom view of the rotating plate of FIG. 1.
Figure 3:
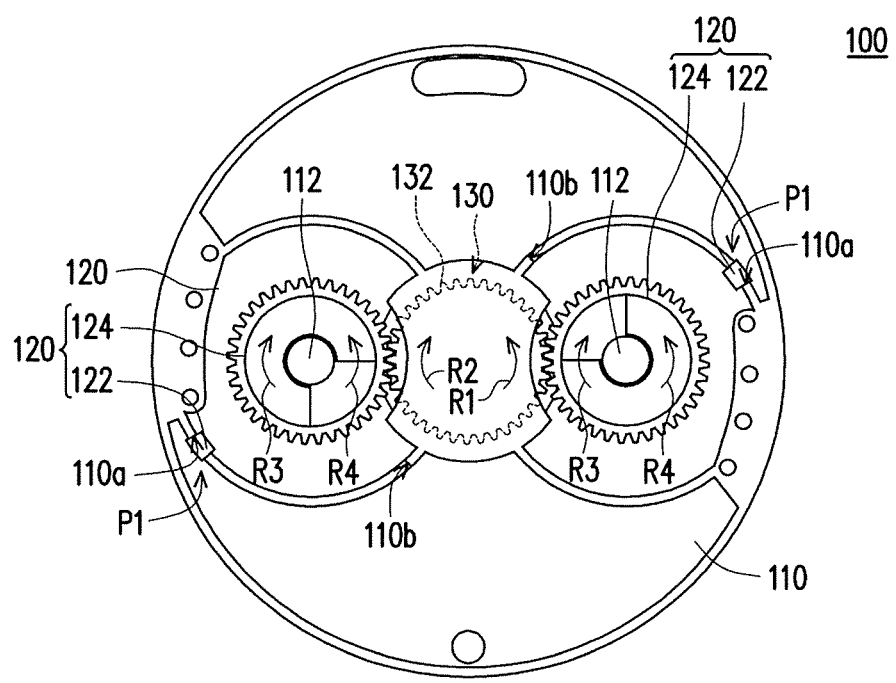
FIG. 3 is a schematic top view showing part of the components in the rotating device of FIG. 1.

FIG. 1 is a schematic top view of a rotating device according to an embodiment of the invention. FIG. 2 is a schematic bottom view of a rotating plate of FIG. 1. FIG. 3 is a schematic top view showing part of the components in the rotating device of FIG. 1. Referring to FIG. 1 to FIG. 3, a rotating device 100 of this embodiment is a blood analyzing device, for example, which includes a carrier 110, at least one rotating plate 120 (two are depicted), and a driving unit 130.

Each rotating plate 120 is rotatably connected with the carrier 110 and is for containing a test liquid (e.g., blood and a corresponding agent). Moreover, each rotating plate 120 has a stopping portion 122, which is a bump, for example. The driving unit 130 includes a rotating member, which is a first gear 132, for example. Each rotating plate 120 has a second gear 124, and the driving unit 130 is engaged with the second gear 124 of each rotating plate 120 through the first gear 132. The rotating member (i.e., the first gear 132) of the driving unit 130 is driven by a driving source (e.g., a motor) to rotate along a first rotation direction R1 or along a second rotation direction R2 opposite to the first rotation direction R1. The rotating plate 120 and the second gear 124 thereof are driven by the rotating member (i.e., the first gear 132) of the driving unit 130 to rotate along a third rotation direction R3 or a fourth rotation direction R4 opposite to the third rotation direction R3. The first rotation direction R1 and the fourth rotation direction R4 are counterclockwise directions while the second rotation direction R2 and the third rotation direction R3 are clockwise directions, for example.

Figure 4A:
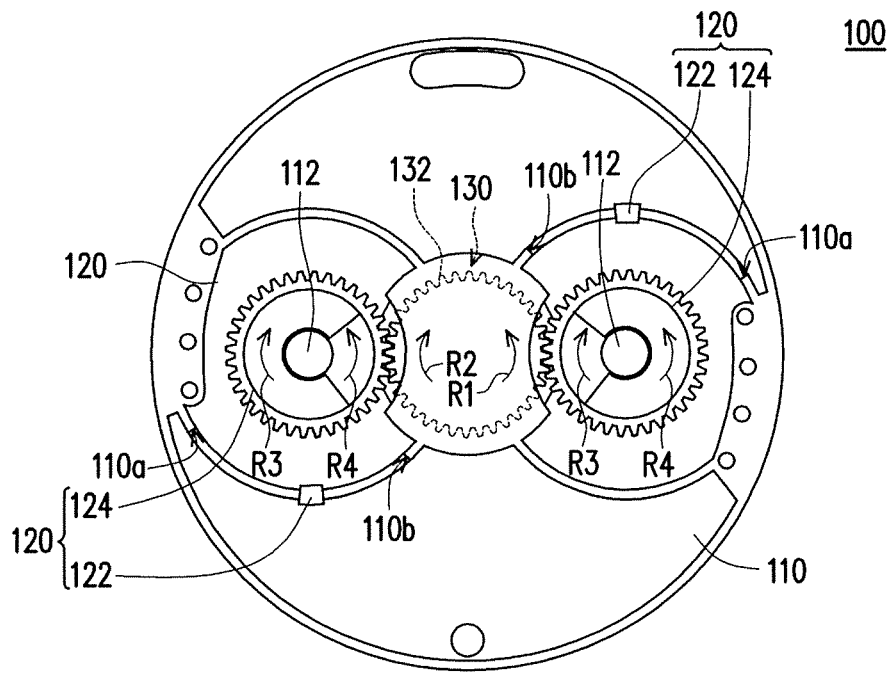
FIG. 4A and FIG. 4B depict that the rotating plates of FIG. 3 rotate relative to the carrier.
Figure 4B:
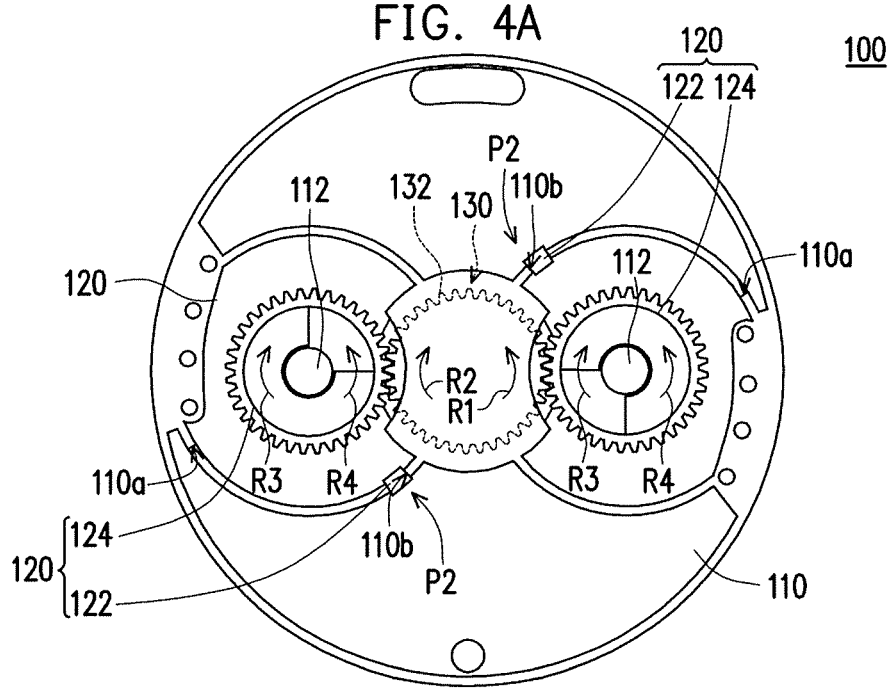

FIG. 4A and FIG. 4B depict that the rotating plates of FIG. 3 rotate relative to the carrier. Referring to FIG. 3, FIG. 4A, and FIG. 4B, the carrier 110 of this embodiment has at least two stopping surfaces (two stopping surfaces 110a and two stopping surfaces 110b are shown in the figures). When the rotating member (i.e., the first gear 132) of the driving unit 130 rotates along the first rotation direction R1 and drives the rotating plate 120 to rotate relative to the carrier 110 along the third rotation direction R3 from the state of FIG. 4A to the state of FIG. 3 so that the stopping portion 122 moves to a first position P1 on the carrier 110 and is against the stopping surface 110a of the carrier 110, the driving unit 130 applies driving force to the pivot portion 112 of the carrier 110 along the first rotation direction R1 through the rotating plate 120 and causes the carrier 110 to rotate along the first rotation direction R1.

In a state where the relative positions of the rotating plates 120 and the carrier 110 are as shown in FIG. 3, when the carrier 110 rotates along the first rotation direction R1 and the rotating member (i.e., the first gear 132) of the driving unit 130 applies driving force to the rotating plate 120 along the second rotation direction R2, since the carrier 110 has a rotational inertia, the rotating plate 120 rotates relative to the carrier 110 along the fourth rotation direction R4 so that the stopping portion 122 moves from the first position P1 as shown in FIG. 3 to a second position P2 on the carrier 110 as shown in FIG. 4B and is against the stopping surface 110b of the carrier 110, and the driving unit 130 applies driving force to the pivot portion 112 of the carrier 110 along the second rotation direction R2 through the rotating plate 120 and causes the carrier 110 to rotate along the second rotation direction R2.

Likewise, in a state where the relative positions of the rotating plates 120 and the carrier 110 are as shown in FIG. 4B, when the carrier 110 rotates along the second rotation direction R2 and the rotating member (i.e., the first gear 132) of the driving unit 130 applies driving force to the rotating plate 120 along the first rotation direction R1, since the carrier 110 has the rotational inertia, the rotating plate 120 rotates relative to the carrier 110 along the third rotation direction R3 so that the stopping portion 122 moves from the second position P2 as shown in FIG. 4B to the first position P1 as shown in FIG. 3 and is against the stopping surface 110a of the carrier 110. At the moment, the driving unit 130 again applies driving force to the carrier 110 along the first rotation direction R1 through the rotating plate 120 and causes the carrier 110 to rotate along the first rotation direction R1.

As described above, the driving unit 130 drives the rotating plate 120 to rotate and interfere with the carrier 110 as shown in FIG. 3 or FIG. 4B, and drives the carrier 110 to rotate through the interference between the rotating plate 120 and the carrier 110. Since the carrier 110 has the rotational inertia when rotating, when the driving unit 130 applies driving force to the rotating plate 120 in a direction opposite to the rotation direction of the carrier 110, the rotating plate 120 and the carrier 110 rotate relative to each other to change the rotation direction of the rotating plate 120 on the carrier 110. Thus, the user is not required to stop the rotation of the carrier 110 to manually change the rotation direction of the rotating plate 120. Accordingly, the working efficiency is improved. In addition, the user does not need to dispose an additional driving source for independently driving the rotating plate 120 on the carrier 110 to rotate. Therefore, equipment costs are reduced. Although two rotating plates 120 are depicted in FIG. 3, the invention is not intended to limit the number of the rotating plates 120, the pivot portions 112 and the stopping portions 122, which may be adjusted according to the requirements of design.

In this embodiment, the driving unit 130 applies the driving force along the first rotation direction R1 and the second rotation direction R2 alternately, for example, such that the rotation direction of the rotating plate 120 is constantly changed between the state of FIG. 3 and the state of FIG. 4B during the rotation of the carrier 110, so as to improve the speed of mixing the blood and the agent.

In this embodiment, the interference between the stopping portion 122 of each rotating plate 120 and the corresponding two stopping surfaces 110a and 110b limits a range of rotation of the rotating plate 120 with respect to the carrier 110, so as to change the rotation direction of the rotating plate 120 to predetermined directions. In addition, other designs may be used as appropriate to increase the precision of movement of the rotating plate 120. An example is described below.

Figure 5:
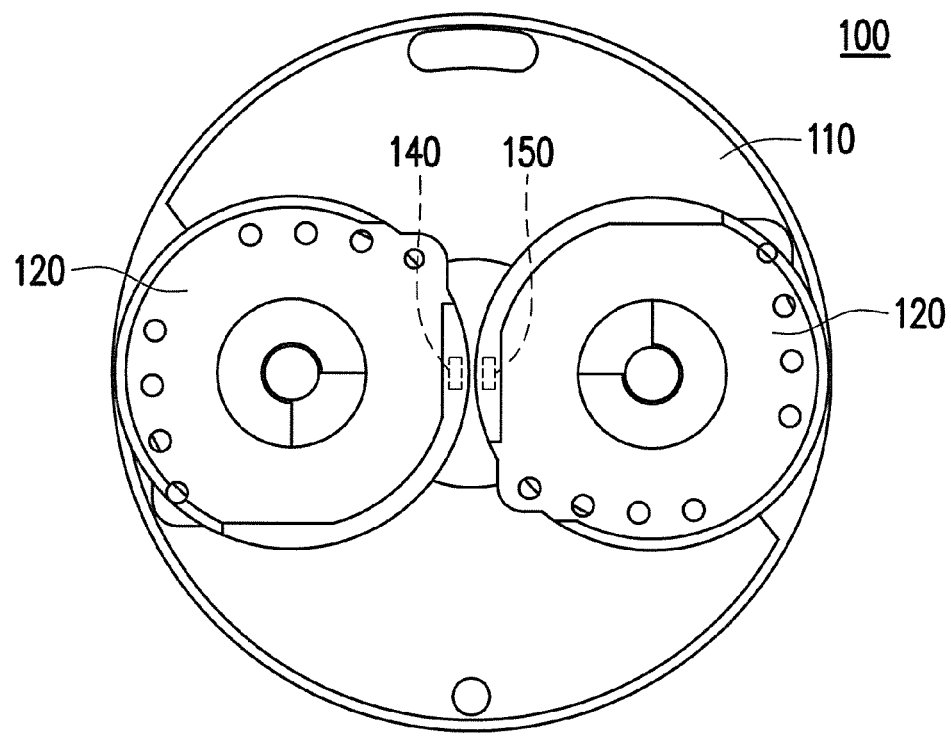
FIG. 5 is a schematic view of the rotating device of FIG. 1 with additional magnetic members.

FIG. 5 is a schematic view of the rotating device of FIG. 1 with additional magnetic members. A difference between the embodiment of FIG. 5 and the embodiment of FIG. 1 is that: the rotating device 100 further includes at least one first magnetic member 140 (one is depicted) and at least one first attractable member 150 (one is depicted). The first attractable member 150 may be attracted by a magnetic force generated by the first magnetic member 140. The first magnetic member 140 may be a magnet and the first attractable member 150 may be a magnet or a magnetic material attractable by the magnet. The first magnetic member 140 and the first attractable member 150 are disposed on the two rotating plates 120 respectively. When the stopping portion 122 of each rotating plate 120 is at the first position P1 as shown in FIG. 3, the two rotating plates 120 are positioned by the magnetic force between the first magnetic member 140 and the first attractable member 150. Moreover, a magnetic member may be disposed at other proper positions on each rotating plate 120, such that when the stopping portion 122 of each rotating plate 120 is at the second position P2 as shown in FIG. 4B, the rotating plates 120 are positioned by the magnetic force between the magnetic member and the attractable member.

Figure 6:
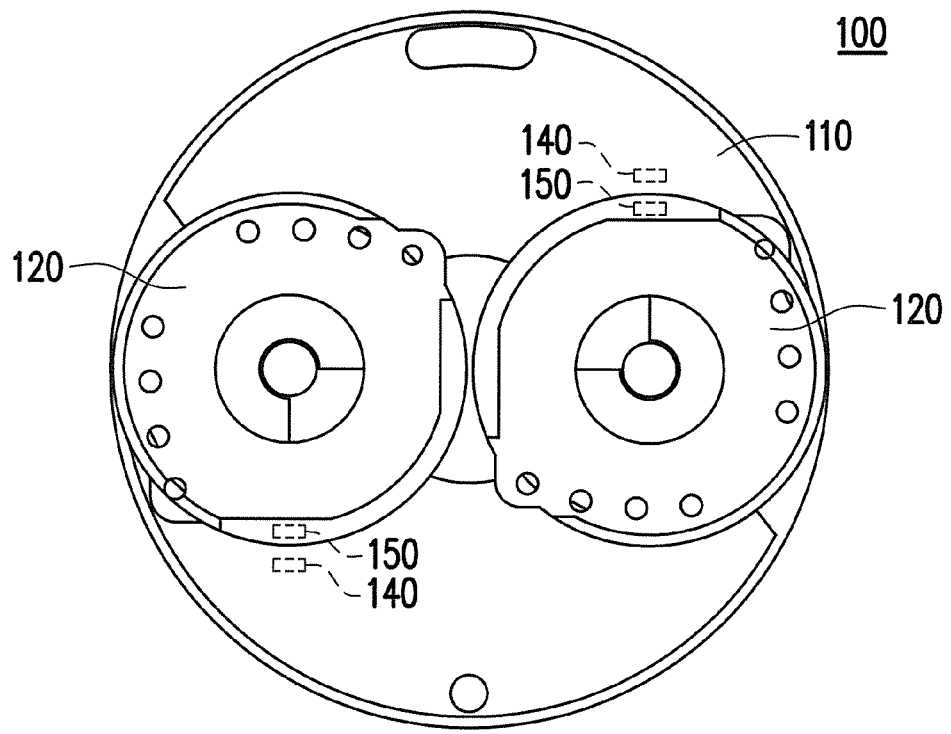
FIG. 6 is a schematic view of the rotating device of FIG. 1 with additional magnetic members.

FIG. 6 is a schematic view of the rotating device of FIG. 1 with additional magnetic members. A difference between the embodiment of FIG. 6 and the embodiment of FIG. 5 is that: the first magnetic member 140 and the first attractable member 150 are disposed on the carrier 110 and the rotating plate 120 respectively. When the stopping portion 122 of each rotating plate 120 is at the first position P1 as shown in FIG. 3, each rotating plate 120 is positioned by the magnetic force between the first magnetic member 140 and the first attractable member 150. Moreover, a magnetic member may be disposed at other proper positions on each rotating plate 120 and the carrier 110, such that when the stopping portion 122 of each rotating plate 120 is at the second position P2 as shown in FIG. 4B, the rotating plate 120 is positioned by the magnetic force between the magnetic member and the attractable member.

Figure 7A:
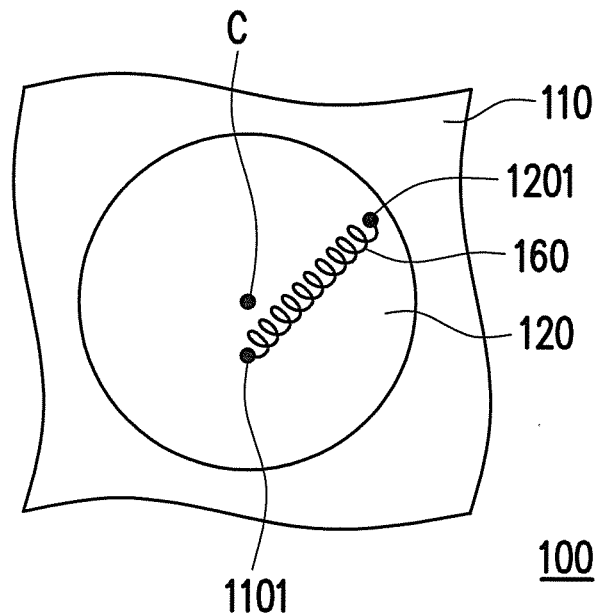
FIG. 7A to FIG. 7C are schematic views of the rotating device of FIG. 1 with an additional elastic member.
Figure 7B:
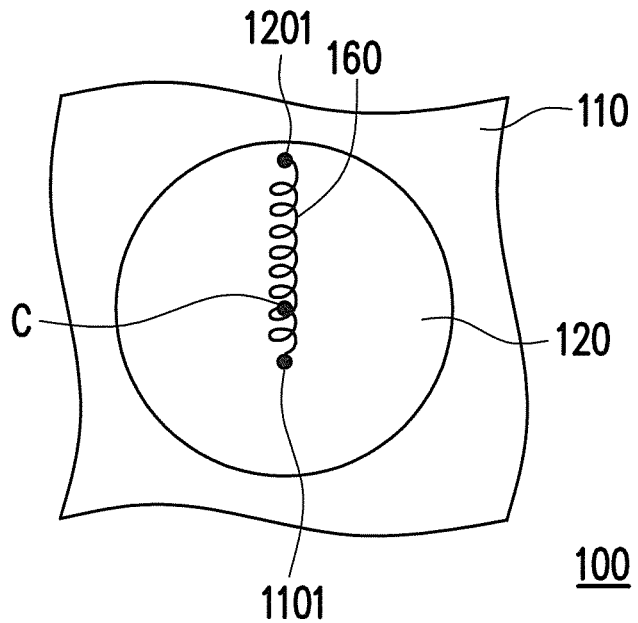
Figure 7C:
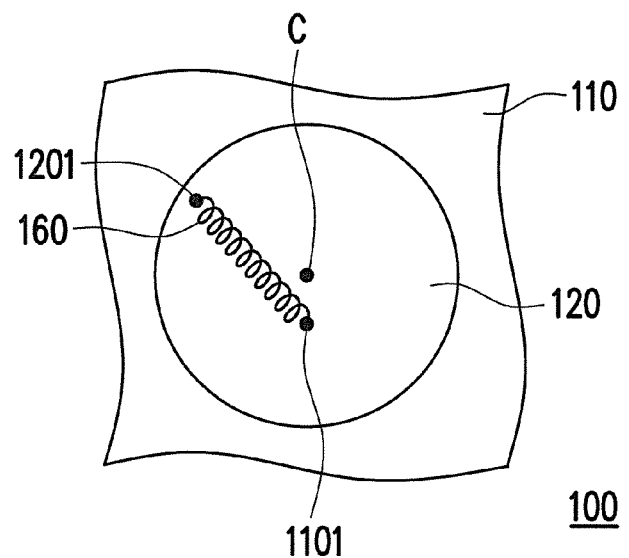

FIG. 7A to FIG. 7C are schematic views of the rotating device of FIG. 1 with an additional elastic member. A difference between the embodiment of FIG. 7A to FIG. 7C and the embodiment of FIG. 1 is that: the rotating device 100 further includes an elastic member 160. The elastic member 160 is a spring, for example, and is connected between a connection point 1101 of the carrier 110 and a connection point 1201 of the rotating plate 120, wherein the connection point 1101 of the carrier 110 deviates from a rotation center C of the rotating plate 120. When the stopping portion 122 of the rotating plate 120 is at the first position P1 as shown in FIG. 3 or the second position P2 as shown in FIG. 4B, the elastic member 160 is in a stretched state as shown in FIG. 7A or FIG. 7C and positions the rotating plate 120 by an elastic force. When the stopping portion 122 of the rotating plate 120 is located between the first position P1 and the second position P2 as shown in FIG. 4A, the elastic member 160 is further stretched as shown in FIG. 7B and causes the rotating plate 120 to rotate by the elastic force, such that the stopping portion 122 moves toward the first position P1 or the second position P2.

Figure 8:
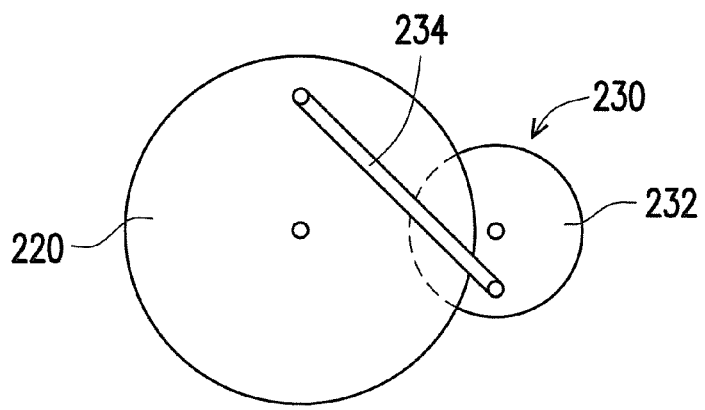
FIG. 8 is a schematic view showing a partial structure of the rotating device according to another embodiment of the invention.

Nevertheless, the invention is not intended to limit how the driving unit drives the rotating plate. An example is described below with reference to the following figures. FIG. 8 is a schematic view showing a partial structure of the rotating device according to another embodiment of the invention. In the embodiment of FIG. 8, a driving unit 230 and a rotating plate 220 have functions similar to those of the driving unit 130 and the rotating plate 120 of FIG. 3. Thus, details thereof are not repeated hereinafter. A difference between the embodiment of FIG. 8 and the embodiment of FIG. 3 is that: the driving unit 230 includes a linking rod 234 with two ends pivotally connected with a rotating member 232 of the driving unit 230 and the rotating plate 220 respectively for causing the rotating plate 220 to rotate when the rotating member 232 rotates.

Figure 9:
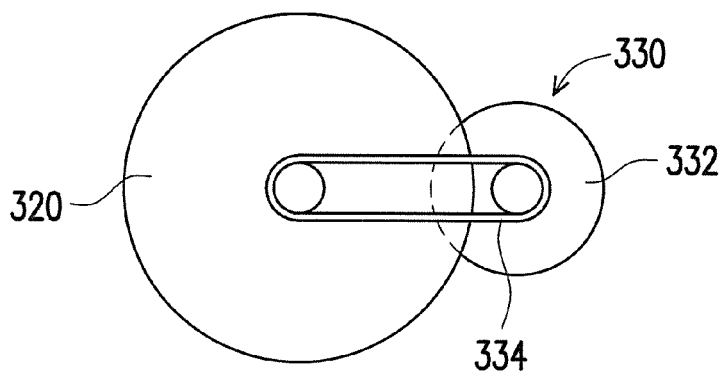
FIG. 9 is a schematic view showing a partial structure of the rotating device according to another embodiment of the invention.

FIG. 9 is a schematic view showing a partial structure of the rotating device according to another embodiment of the invention. In the embodiment of FIG. 9, a driving unit 330 and a rotating plate 320 have functions similar to those of the driving unit 130 and the rotating plate 120 of FIG. 3. Thus, details thereof are not repeated hereinafter. A difference between the embodiment of FIG. 9 and the embodiment of FIG. 3 is that: the driving unit 330 includes a transmission belt 334 connected between the rotating member 332 of the driving unit 330 and the rotating plate 320 for causing the rotating plate 320 to rotate when the rotating member 332 rotates.

Figure 10:
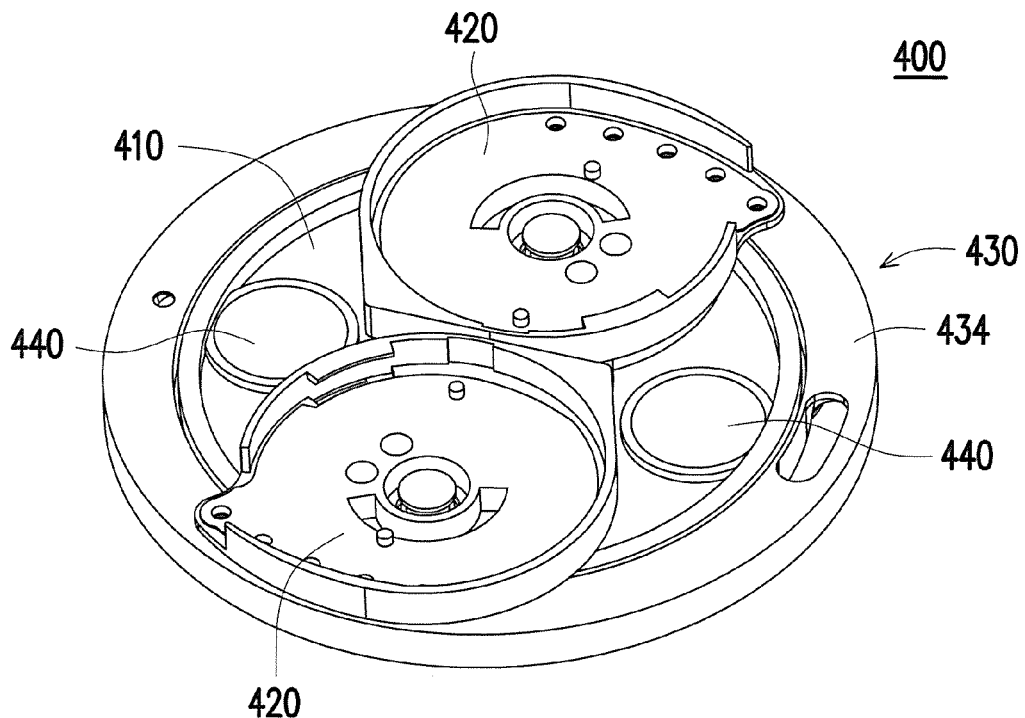
FIG. 10 is a schematic perspective view of the rotating device according to another embodiment of the invention.
Figure 11:
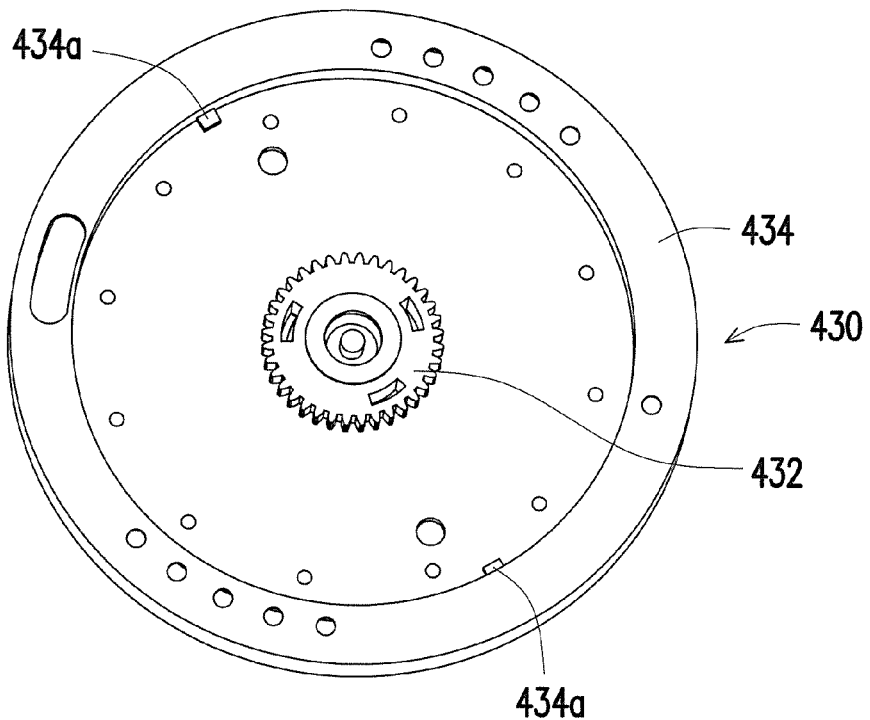
FIG. 11 is a schematic perspective view of the driving unit of FIG. 10.
Figure 12:
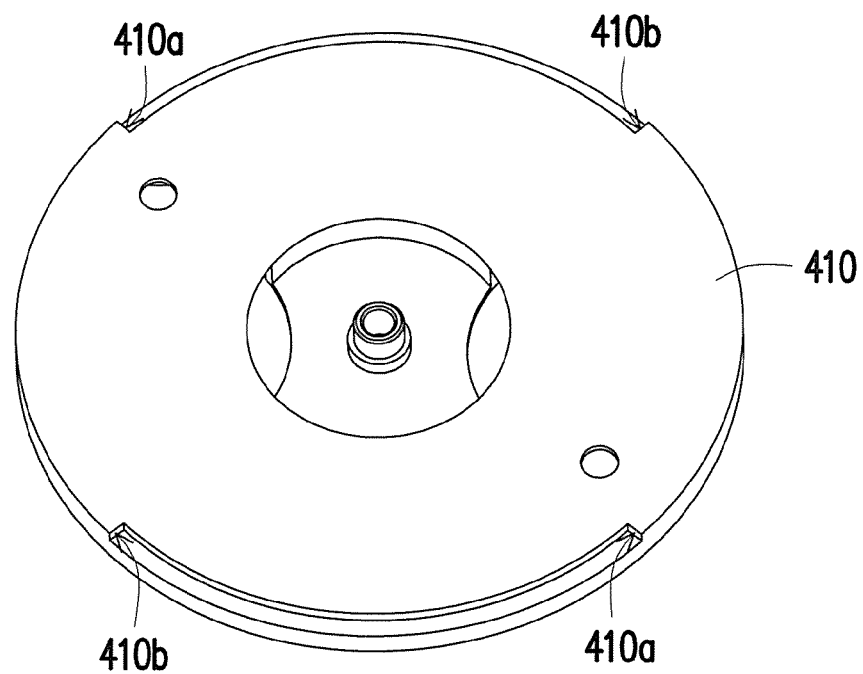
FIG. 12 is a schematic perspective view of the carrier of FIG. 10 from another perspective.

FIG. 10 is a schematic perspective view of the rotating device according to another embodiment of the invention. FIG. 11 is a schematic perspective view of the driving unit of FIG. 10. FIG. 12 is a schematic perspective view of the carrier of FIG. 10 from another perspective. In a rotating device 400 of FIG. 10 to FIG. 12, a carrier 410, a stopping surface 410a, a stopping surface 410b, a rotating plate 420, a driving unit 430, and a rotating member (i.e., a first gear 432) have a configuration and functions similar to the configuration and functions of the carrier 110, the stopping surface 110a, the stopping surface 110b, the rotating plate 120, the driving unit 130, and the rotating member (i.e., the first gear 132) of FIG. 1 to FIG. 7C. Thus, details thereof are not repeated hereinafter. A difference between the rotating device 400 and the rotating device 100 is that: the driving unit 430 includes a base 434 connected with the rotating member (i.e., the first gear 432), and the stopping portion 434a is located on the base 434, unlike the stopping portion 122 of FIG. 2 which is located on the rotating plate 120. That is, the driving unit 430 of this embodiment causes the carrier 410 to rotate through the interference between the stopping portion 434a on the base 434 and the stopping surfaces 410a and 410b of the carrier 410, unlike the driving unit 130 of FIG. 2 and FIG. 3 which causes the carrier 110 to rotate through the interference between the stopping portion 122 on the rotating plate 120 and the stopping surfaces 110a and 110b of the carrier 110.

Figure 13:
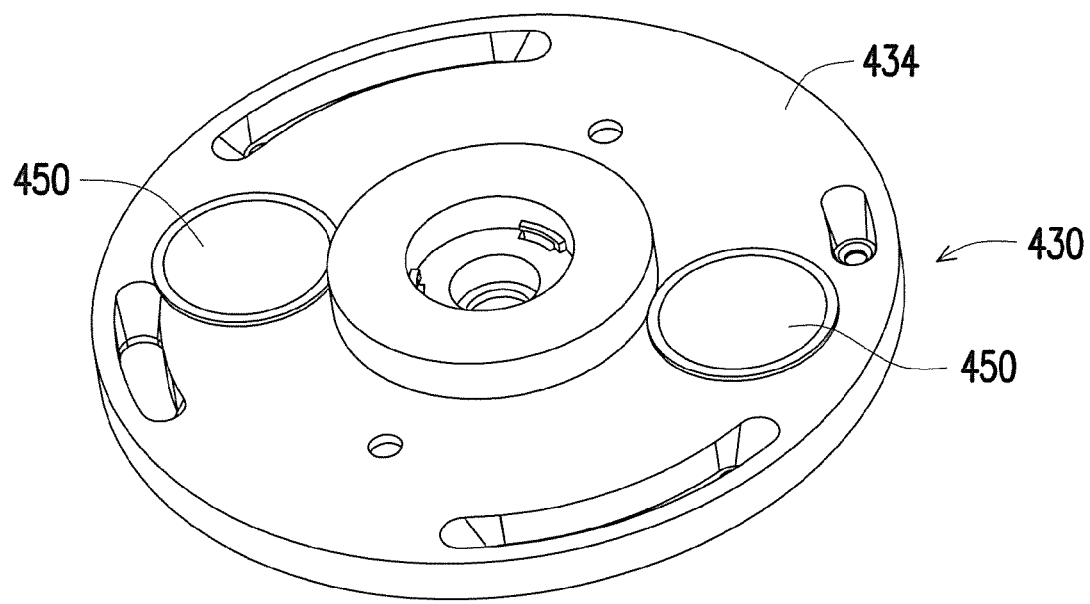
FIG. 13 is a schematic perspective view of the driving unit of FIG. 10 from another perspective.

FIG. 13 is a schematic perspective view of the driving unit of FIG. 10 from another perspective. Another difference between the rotating device 400 and the rotating device 100 is that: a first magnetic member 440 and a first attractable member 450 are disposed on the carrier 410 and the base 434 respectively as shown in FIG. 10 and FIG. 13, unlike the first magnetic member 140 and the first attractable member 150 of FIG. 5 which are disposed on two rotating plates 120 respectively and unlike the first magnetic member 140 and the first attractable member 150 of FIG. 6 which are disposed on the rotating plate 120 and the carrier 110 respectively. When the stopping portion 434a (as shown in FIG. 11) on the base 434 is at the first position and is against the stopping surface 410a (as shown in FIG. 12) of the carrier 410 or is at the second position and is against the stopping surface 410b (as shown in FIG. 12) of the carrier 410, the carrier 410 and the base 434 are positioned by the magnetic force between the first magnetic member 440 and the first attractable member 450.

To sum up, in the rotating device of the invention, the driving unit drives the rotating plate to rotate and interfere with the carrier, and drives the carrier to rotate through interference between the rotating plate and the carrier or interference between the base of the driving unit and the carrier. Since the carrier has a rotational inertia when rotating, when the driving unit applies driving force to the rotating plate in the direction opposite to the rotation direction of the carrier, the rotating plate and the carrier rotate relative to each other so as to change the rotation direction of the rotating plate on the carrier. Thus, the user is not required to stop the rotation of the carrier to manually change the rotation direction of the rotating plate. Accordingly, the working efficiency is improved. In addition, the user does not need to dispose an additional driving source for independently driving the rotating plate on the carrier to rotate. Therefore, equipment costs are reduced. Furthermore, the rotating plate or the carrier may be positioned by using the magnetic force generated by the magnetic members or the elastic force of the elastic member, so as to increase the precision of movements of the rotating plate and the carrier.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. A rotating device, comprising:
   a carrier, has at least one pivot portion;
   at least one rotating plate rotatably connected with the at least one pivot portion, wherein a rotating center of the earner is different from a rotating center of the at least one rotating plate; and
   a driving unit connected with the at least one rotating plate, wherein the at least one rotating plate or the driving unit comprises at least one stopping portion for interfering with the earner, the driving unit comprises a rotating member engaged with the at least one rotating plate, and a radius of the at least one rotating plate is larger than a radius of the rotating member, and
   wherein the carrier comprises at least two stopping surfaces, when the at least one stopping portion is at a first position on the carrier, the at least one stopping portion is against one of the at least two stopping surfaces, and when the at least one stopping portion is at a second position on the carrier, the at least one stopping portion is against the other one of the at least two stopping surfaces,
   wherein the rotating member rotates along a first rotation direction to cause the at least one stopping portion to move to the first position, and the rotating member rotates along a second rotation direction to cause the at least one stopping portion to move to the second position.

2. The rotating device according to claim 1, wherein the rotating member comprises a first gear and the at least one rotating plate comprises a second gear, and the first gear is engaged with the second gear.

3. The rotating device according to claim 1, wherein the driving unit comprises a linking rod with two ends pivotally connected with the rotating member and the at least one rotating plate respectively.

4. The rotating device according to claim 1, wherein the driving unit comprises a transmission belt, and the transmission belt is connected between the rotating member and the at least one rotating plate.

5. The rotating device according to claim 1, wherein the driving unit comprises a base, the base is connected with the rotating member.

6. The rotating device according to claim 1, comprising at least one first magnetic member and at least one first attractable member, wherein the at least one first attractable member is attracted by a magnetic force generated by the at least one first magnetic member, the number of the at least one rotating plate is two, the at least one first magnetic member and the at least one first attractable member are disposed on the two rotating plates respectively, and when the at least one stopping portion is at the first position or the second position, the two rotating plates are positioned by the magnetic force between the at least one first magnetic member and the at least one first attractable member.

7. The rotating device according to claim 1, comprising at least one first magnetic member and at least one first attractable member, wherein the at least one first attractable member is attracted by a magnetic force generated by the at least one first magnetic member, the at least one first magnetic member and the at least one first attractable member are disposed on the carrier and the at least one rotating plate respectively.

8. The rotating device according to claim 1, comprising an elastic member, wherein the elastic member is connected between the earner and the at least one rotating plate, and when the at least one stopping portion is at the first position or the second position, an elastic force of the elastic member positions the at least one rotating plate and when the at least one stopping portion is located between the first position and the second position, the elastic force of the elastic member causes the at least one rotating plate to rotate so that the at least one stopping portion moves toward the first position or the second position.

9. The rotating device according to claim 5, wherein the base comprises a recess for accommodating the carrier.

10. The rotating device according to claim 5, wherein the at least one stopping portion is located on the base.

11. The rotating device according to claim 9, wherein the at least one stopping portion is located on a bottom of the recess.

12. The rotating device according to claim 5, comprising at least one first magnetic member and at least one first attractable member, wherein the at least one first magnetic member and the at least one first attractable member are disposed on the carrier and the base respectively.

* * * * *